United States Patent [19]
Ordman

[11] Patent Number: 5,558,870
[45] Date of Patent: Sep. 24, 1996

[54] METHOD FOR MAINTAINING A CONTINUOUSLY-SATURATED LEVEL OF ASCORBIC ACID IN A PATIENT'S BODY

[75] Inventor: Alfred B. Ordman, Beloit, Wis.

[73] Assignee: Harry M. Weiss, Phoenix, Ariz.; a part interest

[21] Appl. No.: 317,311

[22] Filed: Oct. 3, 1994

[51] Int. Cl.$^6$ ........................................ A61K 9/20
[52] U.S. Cl. ............................... 424/400; 424/464
[58] Field of Search ........................... 514/474, 161, 514/400, 464

[56] References Cited

U.S. PATENT DOCUMENTS 4,160,696 7/1979 Wu ................................. 426/231
5,070,085 12/1991 Markham ........................ 514/474

OTHER PUBLICATIONS

*Merck Manual of Diagnosis and Therapy;* Berkow, R. ed., Merck & Co., Inc., Rahway N.J., 1977, pp. 1168, 2075, 1119.
Pelletier, *J. Lab. & Clin. Med.,* vol. 72(4), Oct., 1968, pp. 674–679.
Hughes, R. E; *Analyst,* vol. 89, pp. 618–620, 1963.
Davies, M. B. et al., "Vitamin C: Its Chemistry and ...," Ryl Soc. of Chem. pp. 7–25, 1991.
Stare, F. J. and I. M. Stare, "Charles Glen King, 1896–1988," J. Nutr., 118:1272–7, 1988.
Roig, M. G. et al., "L–Ascorbic Acid: an Overview," Int. J. Food Sci., 44:59–72, 1993.
Block, G., "Vitamin C, Cancer and Aging," Age, vol. 16, pp. 55–58, 1993.
Marwick, C., "Cancer Institute Takes a Look at Ascorbic Acid," JAMA, 264:1926, 1990.
Wittes, R. E., "Vitamin C and Cancer," New Eng. J. Med., 312:178–9, 1985.
Burr, M. L. et al., "Vitamin C and Cholesterol ..," Human Nutr., 39c:387–8, 1985.
Kimura, H. et al., "Dietary Ascorbic Acid Depresses ...," J. Nutr., 122:1904–9, 1992.
Uchida, K. et al., "Effect of Vitamin C Depletion ...," Nutr., 120:1140–7, 1990.
Blanchard, J. et al., "Comparison of Plasma ...," Eur. J. Clin. Nutr., 43:97–106, 1989.
Chavance, M. et al., "Vitamin Status ...," Eur. J. Clin. Nutr., 43:827–35, 1989.
Vallance, S., "Platelelts, Leukocytes and Buffy Layers ...," Hum. Nutr., 40c:35–41, 1986.
Vojdani, A. et al., "In Vivo Effect of Ascorbic ...," Nutr. Res., 13:753–764, 1993.
Pryor, W. A., "The Formation of Free Rad...," Photochem. Photobiol., 28:787–801, 1978.
Harman, D., "The Aging Process," Proc. Natl. Acad. Sci. USA, 78:7128, 1981.
Tappel, A. L., "Vitamin E as the Biological ...," Vitam. Horm., 20:493–510, 1962.
Niki E. et al., "Inhibition of Oxidation ...," J. Biol. Chem., 259:4177–4182, 1984.

(List continued on next page.)

*Primary Examiner*—Thurman K. Page
*Attorney, Agent, or Firm*—Harry M. Weiss; Antonio R. Durando

[57] ABSTRACT

A method of administration of vitamin C to ensure that a continuously-saturated level is produced in the body of a taker. A dose of about 500 mg taken approximately every 12 hours produces a continuously-detectable level of vitamin C in the urine of an average healthy person, which corresponds to a sufficiently high pool of ascorbic acid in the body to provide anti-oxidant protection. The minimum dosage and regimen found to be effective are respectively substantially higher than the U.S. recommended daily allowance and more frequent than administration rates previously used in clinical trials. Also claimed are kits that permit individuals to monitor for elevated urinary excretion of useful substances which are water soluble, excreted in urine, and non-toxic at physiologically beneficial levels, such that optimal dosages and regimens can be determined.

2 Claims, 7 Drawing Sheets

OTHER PUBLICATIONS

Harman, D., "Free Raidcal Theory . . . ," Lipofuscin–1987: State of the Art, pp. 3–21, 1988.

Olson, J. A. and R. E. Hodges, "The Scientific Basis . . . ," Nutr. Today, 20:14–15, 1985.

Blanchard, J. et al., "Effects of Age . . . ," Eur. J. Clin. Nutr., 44:447–460, 1990.

Omaye, T. S. et al., "Selected Methods . . . ," Methods in Enzymology, 62:3–11, 1979.

METHOD FOR MAINTAINING A CONTINUOUSLY-SATURATED LEVEL OF ASCORBIC ACID IN A PATIENT'S BODY

BACKGROUND OF THE INVENTION

1. Field of the Invention

This invention is related in general to the oral administration of water-soluble medication and nutritional supplements. In particular, it describes a method for optimal intake of vitamin C.

2. Description of the Related Art

Vitamin C, ascorbic acid, has long been known to prevent scurvy and more recently has been shown to have an effect on the healing of wounds, the health of gums, and the strength of bones through the stabilization of collagen. See Davies, M. B. et al., "Vitamin C: Its Chemistry and Biochemistry," Cambridge, Royal Society of Chemistry, 1991, pp. 7–25; Stare, F. J. and I. M. Stare, "Charles Glen King, 1896–1988," J. Nutr., 118:1272-7, 1988; and Roig, M. G. et al., "L-Ascorbic Acid: an Overview," Tnt. J. Food Sci. Nutr., 44:59–72, 1993. However, other possible health benefits, including prevention of cancer (see Roig, supra; Block G., "Vitamin C, Cancer and Aging," Age, 16:55–8, 1993; Marwick, C., "Cancer institute Takes a Look at Ascorbic Acid," JAMA, 264:1926, 1990; and Wittes, R. E., "Vitamin C and Cancer," New Engl. J. Med., 312:178–9, 1985), prevention of heart attacks and reduction of cholesterol (Burr, M. L. et al., "Incidence for Premature Rupture of Membranes in Pregnant Women with Low Leukocyte Levels of Vitamin C," Eur. J Clin. Nutr., 39c:387–8, 1985; Kimura, H. et al., "Dietary Ascorbic Acid Depresses Plasma and Low Density Lipoprotein Lipid Peroxidation in Genetically Scorbutic Rats," J. Nutr., 122:1904–9, 1992; and Uchida, K. et al., "Effect of Vitamin C Depletion on Serum Cholesterol and Lipoprotein Levels in ODS (od/od) Rats Unable to Synthesize Ascorbic Acid," J. Nutr., 120:1140–7, 1990), and as a boost to the immune system to prevent colds (Blanchard, J. et al. "Comparison of Plasma, Mononuclear and Polymorphonuclear Leukocyte Vitamin C Levels in Young and Elderly Women during Depletion and Supplementation," Eur J. Clin Nutr., 43:97–106, 1989; Chavance, M. et al. "Vitamin Status, Immunity and Infections in an Elderly Population," Eur. J. Clin. Nutr., 43:827–35, 1989; Vallance, S., "Platelets, Leukocytes and Buffy Layer Vitamin C After Surgery," Hum. Nutr., 40c:35–41, 1986: and Vojdani, A. and M. Ghoneum, "In Vivo Effect of Ascorbic Acid Enhancement of Human Natural Killer Cell Activity," Nutr. Res., 13:753, 1993), remain controversial.

The "free radical theory of aging" has been postulated to explain age-related cell damage in animals and plants. See Pryor, W. A., "The Formation of Free Radicals and the Consequences of their Reactions in Vivo," Photochem. Photobiol., 28:787–801, 1978; and Harman, D., "The Aging Process," Proc. Natl. Acad. Sci. USA, 78:7124–7128, 1981. Vitamin C appears to play a synergistic role with vitamin E in providing essential anti-oxidant protection (Tappel, A. L., "Vitamin E as the Biological Lipid Antioxidant," Vitam. Horm., 20:493–510, 1962; and Niki E. et al., "Inhibition of Oxidation of Methyl-Linoleate in Solution by Vitamin E and Vitamin C," J. Biol. Chem., 259:4177–4182, 1984). Given the large number of "free radical" diseases, it is reasonable to assume that taking an optimal dose of vitamin C could be extremely beneficial, as suggested by Block, G., supra, and by Harman, D. in "Free Radical Theory of Aging: Current Status," Lipofuscin 1987: State of the Art, edited by I. Zs.-Nagy, New York, Elsevier, 1988, pp. 3–21. With around 20 million people in the U.S. taking daily supplements of Vitamin C, it is appropriate to ask what an optimal dosage would be.

Unfortunately, the optimal dose of vitamin C is not established. The recommended daily allowance sufficient to prevent scurvy varies from 30 mg in the United Kingdom to 60 mg in the U.S. and 90 mg in the former Soviet Union. In contrast, mega-doses of up to 16 g per day are suggested to provide additional health benefits.

In fact, the optimal dose of vitamin C depends on many factors. It is water soluble and cannot be stored in the body to any great extent. However, when vitamin C is regularly ingested, a body pool develops, which may become large even though some vitamin C is being excreted in the urine. Thus, it can take months of ascorbic acid deprivation for the body pool to become depleted to the point where symptoms of scurvy appear. Large-dose intake benefits may be small because of finite absorption from the intestine, limited metabolism by the liver, or excretion by the kidney. For example, it has been reported that only about 60% of a 500 mg dose is normally absorbed into the body of an average person within the first 12 hr after ingestion, while 40% is excreted prior to metabolization (see Olson, J. A., and R. E. Hodges, "The Scientific Basis of the Suggested New RDA Values for Vitamins A and C," Nutr. Today, 20:14–15, 1985). In fact, it has been ascertained that a certain percentage of any dose is always excreted, and that such percentage increases with the dose (see Blanchard, J. et al., "Effects of Age and Intake on Vitamin C Disposition in Females," Eur. J. Clin. Nutr., 44:447–460, 1990).

Without a clear physiological endpoint to measure an optimal dosage or a complete understanding of the functional role of vitamin C, it is unclear how much vitamin C one should take. Because large doses are not entirely absorbed and may even irritate a patient's stomach, and because small doses may be insufficient to provide sufficient anti-oxidant protection, there exists a need to determine a dosage sufficiently large to ensure as large as possible a presence in the body while at the same time minimizing excesses and waste through excretion. This invention provides a method that fulfills this need by ensuring that some excess vitamin C is always present in the urine of a user.

BRIEF SUMMARY OF THE INVENTION

The primary objective of this invention is a dosage and regimen of ascorbic-acid intake that ensures continuously high levels thereof in the body of a user without the need for large excesses at any given time.

Another goal of the invention is an approach to determining optimal intake dosages and regimens for various kinds of water-soluble, urine-excreted, and non-toxic vitamins and other nutritional substances.

Therefore, according to these and other objectives, the present invention consists of a finding that a dose of about 500 mg taken approximately every 12 hours produces a continuously-detectable level of vitamin C in the urine of an average healthy person. If either one of these two conditions is not met, continuous excretion of vitamin C is not maintained, thereby preventing the formation of a sufficiently high pool of ascorbic acid in the body to provide anti-oxidant protection. The minimum dosage and regimen found to be effective are respectively substantially higher than the U.S. recommended daily allowance and more frequent than administration rates previously used in clinical trials. Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

DESCRIPTION OF THE PREFERRED EMBODIMENTS OF THE INVENTION

The present invention amounts to a finding of the minimum rate of intake of ascorbic acid required to provide continuous optimal anti-oxidant protection to an average individual. The invention also discloses a general method for determining such optimal dosages and intake regimens for water-soluble vitamins and other nutritional supplements and medicines that require elevated concentrations in the blood stream for optimal effect.

Because vitamin C has been implicated in a variety of diseases, it has been the subject of frequent clinical studies. These studies have compared subjects taking vitamin C on a "regular daily basis" with those not taking vitamin C. However, because vitamin C is a water-soluble vitamin, high doses are readily excreted in the urine, thereby quickly depleting the system to blood concentrations well below saturation.

With reference to vitamin C, saturation is defined herein as the level in an individual's blood stream above which vitamin C is excreted into the urine. Thus, the work that resulted in this disclosure was undertaken to determine what daily dose of vitamin C is necessary on average to produce a measurable level of vitamin C excretion in urine; whether a single dose, even a very high one, is sufficient to maintain measurable excretion at all times during an entire 24-hour period; and whether taking a regular daily dose of vitamin C leads to any noticeable change in vitamin C excretion over time.

The following procedures were followed in the experiments that generated the data shown in the figures.

I. Stability of Vitamin C in Water and Urine

To determine whether vitamin C is stable in urine prior to assay, stock solutions of vitamin C in water and in urine were prepared 48, 24, 12, and 0 hours before running standard curves using the DCIP procedure referenced below. Each stock solution contained 125 µg of vitamin C/ml of 5% phosphoric acid in water or urine. The samples were stored in the dark at room temperature. The vitamin C degraded when stored in aqueous solutions of 5% phosphoric acid, but was stable in solutions containing urine in 5% phosphoric acid.

II. Effect of Dose of Vitamin C on Total Urinary Excretion

Figure 1:
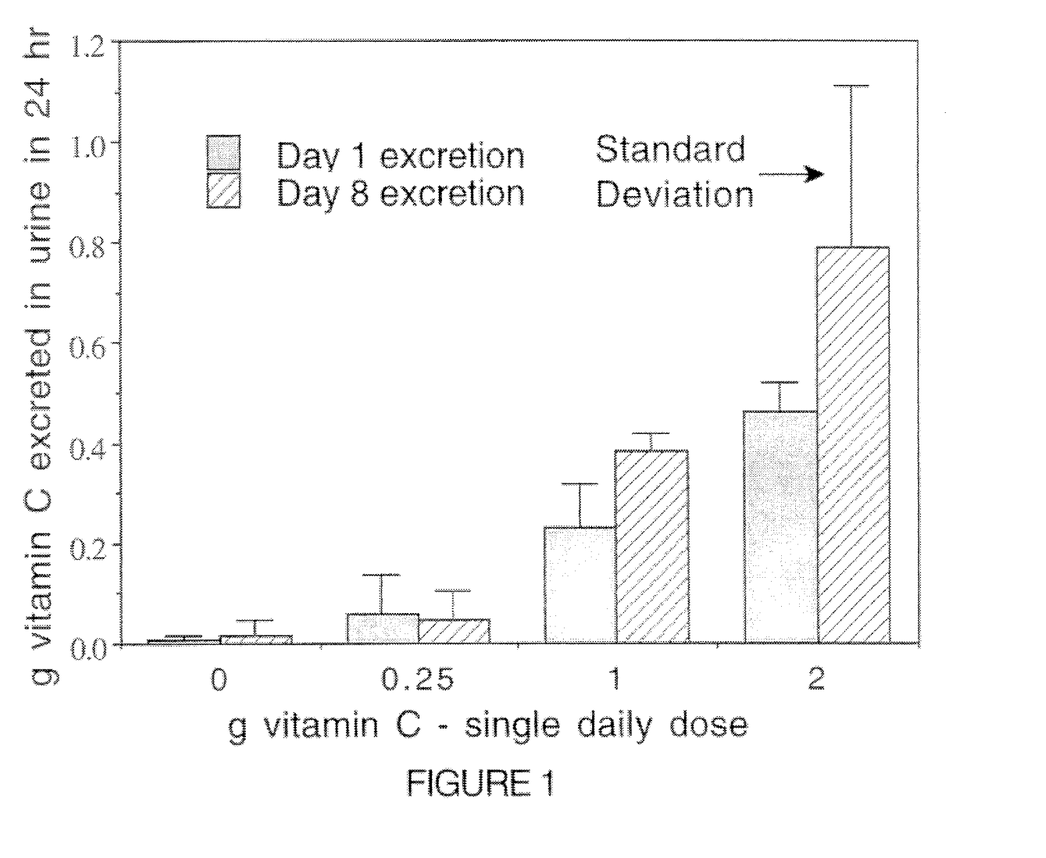
FIG. 1 is an illustration of the relationship between daily doses of vitamin C and total urinary excretion during the 24-hour period following intake.

In order to determine how daily dosages related to total excretion and whether high daily doses would alter the rate of excretion after a week, groups of test subjects took either 0, 0.25, 1, or 2 gram doses of vitamin C at 8 am daily for 8 consecutive days. All urine was collected and pooled on day 1 and on day 8. The concentration was assayed and the total amount of vitamin C excreted during the 24-hour period was determined, as shown in FIG. 1. The figure shows that the rate of urinary excretion of vitamin C increased with increasing daily doses of vitamin C, and that the amount excreted was similar even after taking it for 8 consecutive days.

III. Rate of Excretion of a Single Dose of Vitamin C

Figure 2A:
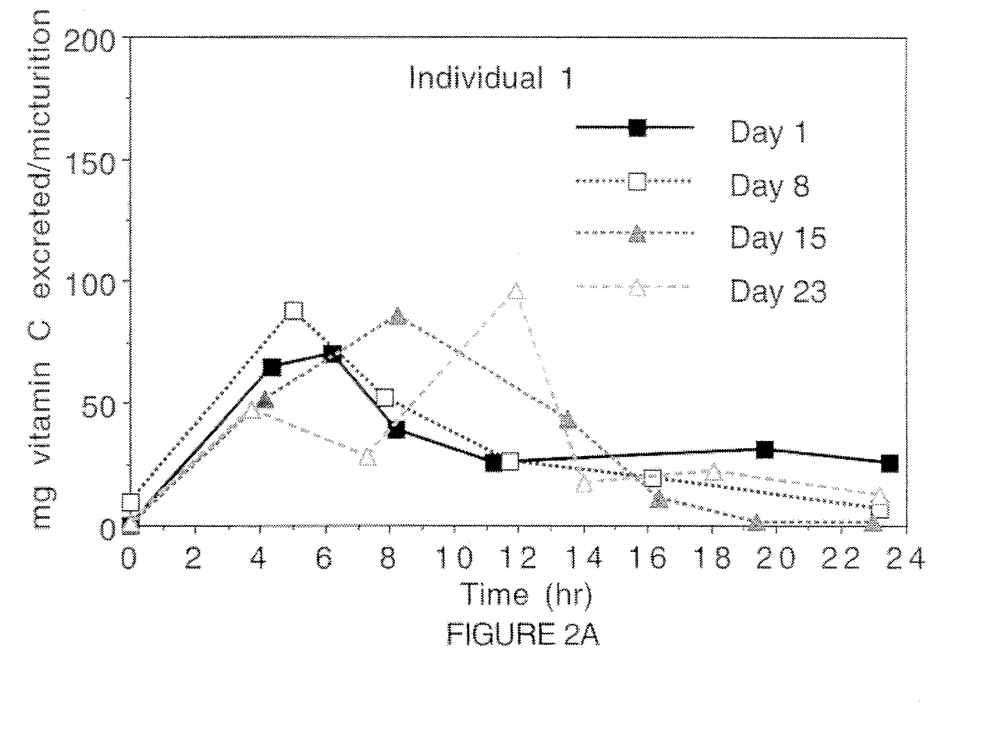
FIGS. 2A, 2B and 2C illustrate the rate of excretion of vitamin C during beginning and end 24-hour periods of separate eight-day cycles of a single daily intake of two grams, for three individual taker's urine (shown separately).
Figure 2B:
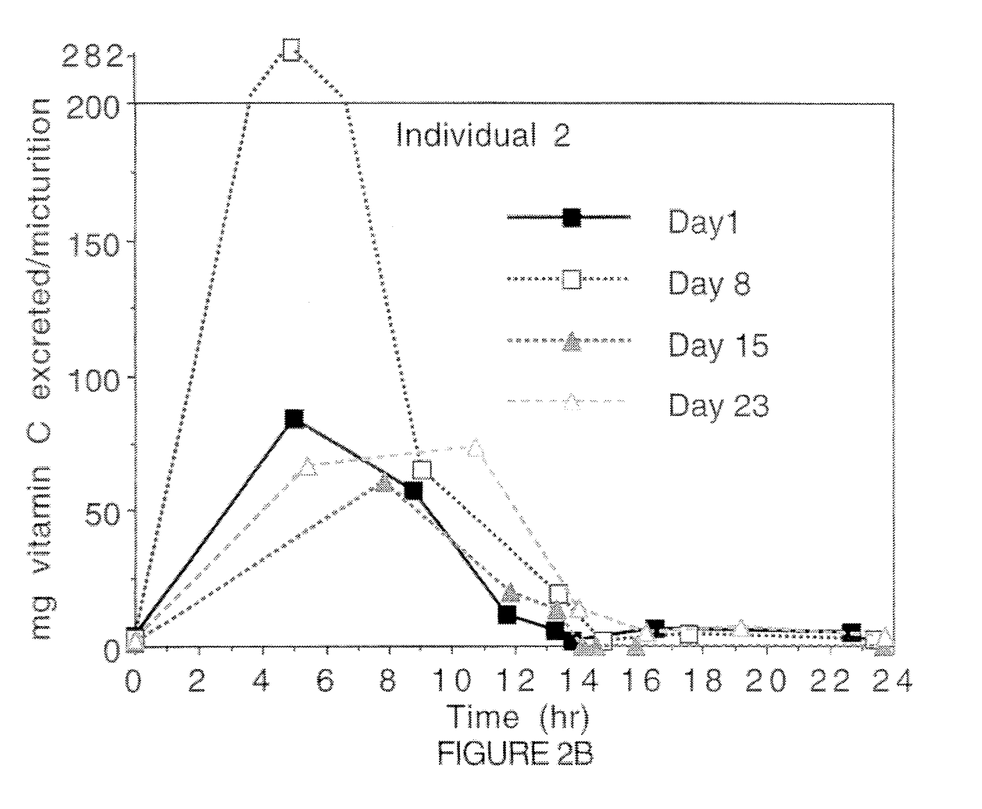
Figure 2C:
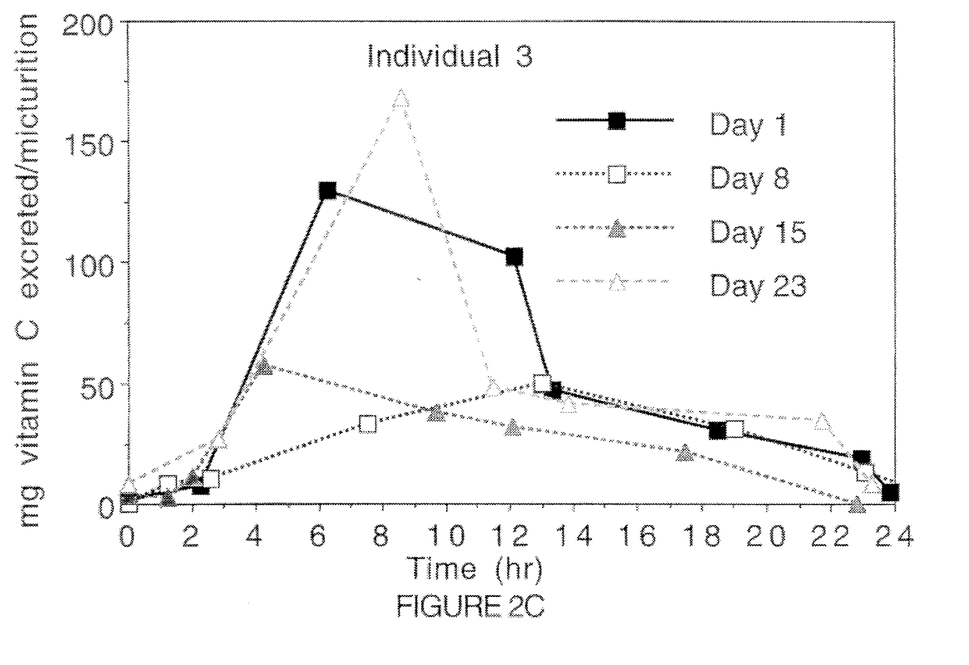

In order to determine how rapidly vitamin C is excreted, several individuals took 2 grams of vitamin C daily (single dose) for 8 consecutive days, and collected samples and measured the volume of every micturition during the first and last day. The experiment was repeated with the same individuals after a seven-day rest. Each sample was analyzed to determine the time period, concentration range, and total urinary excretion of vitamin C. The results are shown in FIG. 2 for three representative individuals. Vitamin C concentration in the urine increased after 4 hours from time of intake and remained elevated for a total of 12 hours, consistent with the hypothesis that vitamin C levels in the body are not elevated for an entire 24 hour period by a single daily dose. However, only a small percentage of the ingested vitamin C was detected in the urine. No noticeable difference in the excretion pattern during the first and last days was observed.

IV. Effect of Twice-Daily Doses of Vitamin C on Urinary Output

Figure 3:
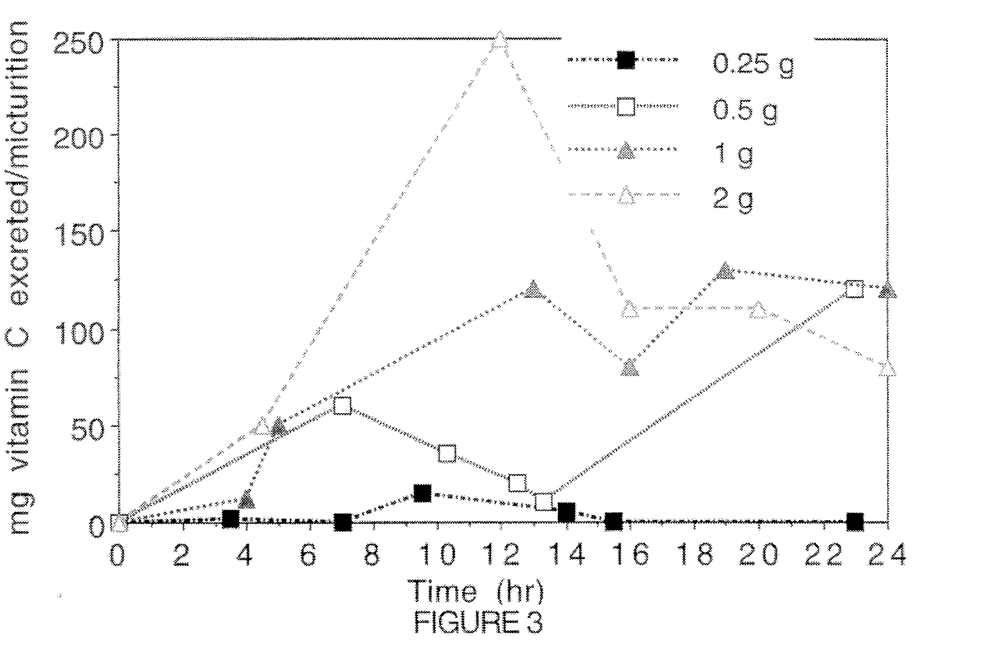
FIG. 3 illustrates the effect of two daily doses of vitamin C for maintaining a measurable excess in a taker's urine.

Because it was found that a single dose of vitamin C elevates urine levels for only 12 hours and that a 500 mg dose is sufficient to provide detectable levels in the urine, one individual took doses from 250 to 2000 mg of vitamin C every 12 hours to determine whether vitamin C levels would remain continuously elevated. FIG. 3 shows that a dose of 250 mg did not cause detectable excretion in amounts exceeding normal quantities, but doses of 500 mg or higher provided continuously-detectable elevated levels of excretion, with higher levels corresponding to higher doses. Twice-daily doses of 500 mg were sufficient to elevate vitamin C in the urine continuously as shown for 5 individuals in FIG. 4. When 500 mg are taken twice daily for a week, vitamin C remains continuously elevated on the first and last day, as shown for two such periods in FIG. 5.

Assay Procedures

Vitamin C was assayed by the 2,6-dichlorophenolindophenol (DCIP) assay (see Omaye, T. S. et al. "Selected Methods for the Determination of Ascorbic Acid in Animal Cells," in Methods Enzymol.: Vitamins and Coenzymes, Vol. 62, edited by McCormick, D. B. and L. D. Wright, New York, Academic Press, 1979, pp. 3–11). Samples diluted to 0–40 µg ascorbic acid with 5% phosphoric acid were assayed in a citrate/acetate buffer by reaction with DCIP, and the color at 520 nm compared with standards. Samples were assayed in duplicate and each experiment was repeated. The ascorbic acid standard was from Gibco Laboratories, and the 500 mg vitamin C pills used were the brand marketed by Leiner Health Products, Inc., of Torrance, Calif., under the trademark "Your Life." The pills were assayed for vitamin C content by extraction by grinding in 5% phosphoric acid and were shown to contain the appropriate quantity of ascorbic acid.

We found that a one-time dose of 500 mg is necessary for detectable excretion in most individuals. As shown in FIG. 1, doses of less than 0.5 g per day caused no detectable vitamin C levels in urine, even when taken for 8 consecutive days. Vitamin C was administered daily to five individuals at 8 am for eight consecutive days. All urine for each individual was collected during the first and last 24-hour periods and the total amount of vitamin C excreted in the urine was determined by DCIP assay. Doses of 500 mg to 2 g resulted in increased levels of urinary vitamin C, so that it was readily detectable, but only for approximately 12 hours even at the highest rate of intake. The figure shows that traces of ascorbic acid may be found in human urine at all times, even when no vitamin C has been administered in pills. A consistently elevated level (greater than the standard deviation of the measurement SD) is found to begin at intake rates between approximately 250 and 500 mg per day, thus showing that lower rates do not produce a saturated condition in the blood stream at all times.

FIG. 2 illustrates the effect of two grams of daily single-dose vitamin C taken orally for eight days, followed by six days with no intake, and then by eight more days of two grams taken daily in a single dose. Each micturition during the first and last 24 hours of each eight-day period was collected and assayed to determine the total mass of vitamin C excreted. FIGS. 2a–2c represent excretion from three different individuals. Despite variations among the different subjects, FIG. 2 shows that taking two grams daily for eight days did not lead to any noticeable difference in the pattern of excretion from day to day for any of the subjects. This demonstrates that even a high single daily dose is inadequate to maintain an elevated rate of urinary excretion of vitamin C on a continuous basis.

In order to achieve such sustained presence of vitamin C in urine, it is instead necessary to take it at least twice daily, as shown in FIG. 3. Different dosages (from 0.25 to 2.0 grams) of vitamin C were administered to a representative subject every 12 hours, at times 0 and 12 hour in the figure, on four separate days of a four week period. The mass of vitamin C present in the urine was measured at every micturition. The individual was tested one day of the week for four consecutive weeks with progressively increasing dosages followed by six-day periods of rest. As illustrated by the figure, taking at least 500 mg twice daily led to continuously elevated levels of vitamin C in the urine tested.

Figure 4:
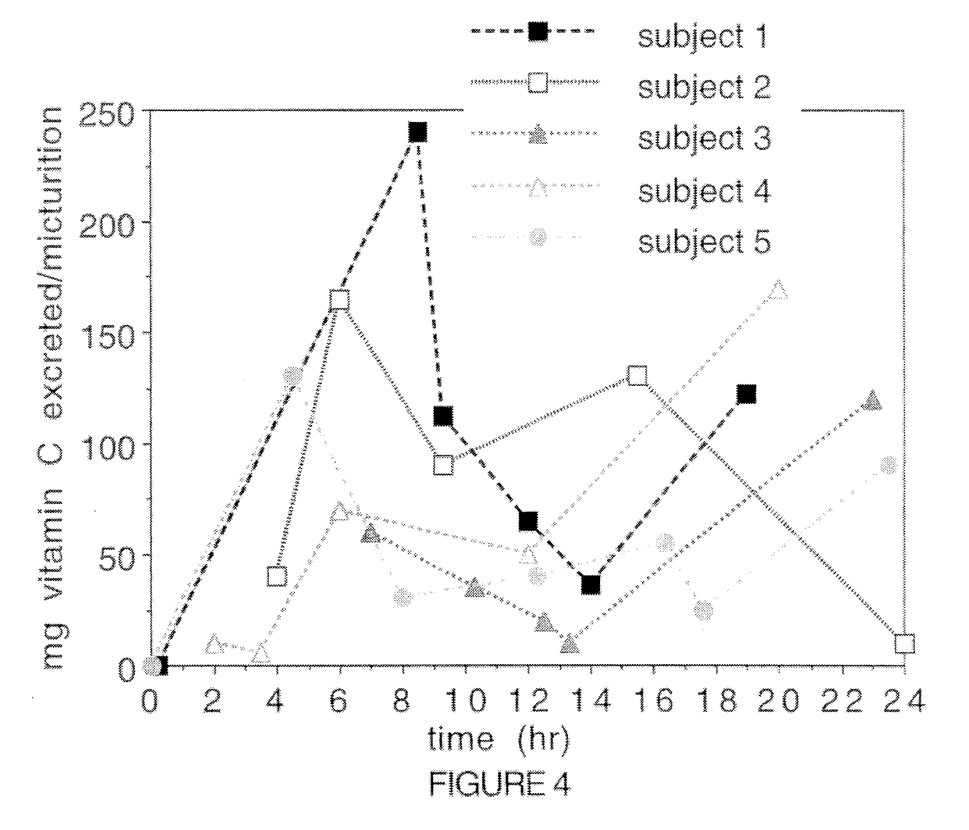
FIG. 4 shows the effect on excretion of vitamin C following a regimen of two daily doses of 500 mg each taken 12 hours apart.
Figure 5:
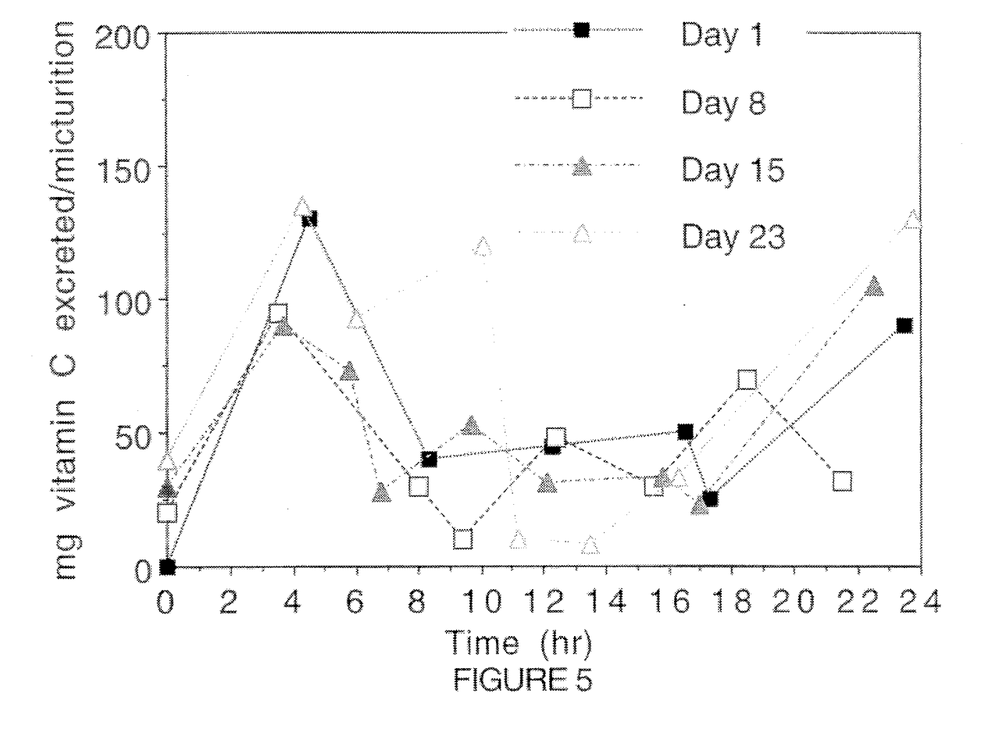
FIG. 5 shows the effect of two daily doses of 500 mg of vitamin C taken for two periods of eight consecutive days each.

FIG. 4 shows the results on five individuals who took 500 mg of vitamin C at time 0 and 12 hour during a 24-hour period. Each micturition during the entire 24 hours was collected and the total mass of vitamin C excreted by each subject was measured by the DCIP assay. In yet another experiment, two daily doses of 0.5 grams of vitamin C were taken daily for 8 days, then no pills were taken for a week, and then 0.5 g daily were taken again for another 8 days. Each micturition during the first and last 24 hr of each 8 day period was collected and assayed to determine the total mass of vitamin C excreted. As seen in FIG. 5, the level of excretion was similar during the first and eighth day of testing (demonstrating that no appreciable cumulative effect occurred).

These results have important implications for dietary purposes and for the design of clinical studies involving vitamin C. First, small doses of vitamin C are unlikely to provide elevated vitamin C levels in the body, particularly in the blood. Therefore, optimal anti-oxidant protection cannot be achieved below a minimum dosage threshold, found to be at about 500 mg per dose. At this point it is still unclear whether doses below 500 mg/dose are absorbed or metabolized, but the evidence clearly supports the fact that at least 500 mg/dose are necessary to saturate the blood sufficiently for vitamin C to appear in the urine.

Second, although 500 mg/dose is sufficient to produce vitamin C excretion, a single dose of even 2 g/day is insufficient to maintain excretion over a 24 hr period. Therefore, if a continuous protective effect is desired or if a study is intended to determine particular protective effects of vitamin C, it is necessary that the vitamin be administered at least every 12 hours.

The precise role of vitamin C in maintaining good health remains to be understood, but a large body of evidence is consistent with the hypothesis that individuals taking doses of vitamin C substantially greater than the USDA Recommended Daily Allowance may have a substantial health benefit. Until the precise role of vitamin C becomes clear, it may be prudent to take a dose which is large enough to produce continuously detectable excretion, but not so large as to cause digestive-system discomfort or other problems. The results of the present work support the conclusion that in order to continuously maintain measurable levels of vitamin C in urine, at least 500 mg of vitamin C should be taken at least twice daily (every 12 hours).

This work also demonstrated a useful tool to determine optimal dosages and regimens for water soluble-substances that are desirable in elevated concentrations in the blood stream. By measuring the concentration of such a substance in urine after ingestion of a predetermined dosage and according to a predetermined regimen, one can find an intake threshold below which the substance is not maintained above saturation, thereby setting a minimum dosage and rate of administration for continuous saturation in the blood pool of an individual. The dosage and regimen for a variety of physiologically and medically useful substances clearly vary for different individuals, depending on many personal characteristics such as age, weight, health, and gender. For substances like nutritional supplements, such as vitamins and minerals, and medicines, such as aspirin, which are water-soluble, are excreted in urine, and are non-toxic at physiologically beneficial levels, monitoring detectable urinary excretion is a means to establish a potentially medically and/or nutritionally useful dosage and regimen. The method involves taking different dosages of substance at different frequencies and testing the urine to determine whether the substance is present in every micturition.

This method could also involve a variety of products specific to the substance being tested. For example, test strips containing individual pads of reactive materials which could be used to check a urine specimen to determine whether a detectable quantity of a particular substance, such as vitamin C, salicylic acid, cystiene, zinc, or selenium, is present. Similarly, dropper kits would permit a person to add drops of certain substances to a urine specimen to determine whether a given substance is present in the urine at a detectable concentration.

For example, a kit for determining whether an individual is taking a sufficient amount of vitamin C for a significant excess to be detected in the urine could consist of the following components:

1. A dropper bottle, labelled Acid, containing a given quantity, such as 10 ml, of 10% phosphoric acid, fitted with a dropper graduated at 0.6 ml.
2. A dropper bottle, labelled Buffer, containing a commensurate quantity, such as 10 ml, of citrate/acetate buffer, pH 4.15 (made with 2.2 g of trisodium citrate dihydrate), fitted with a dropper graduated at 0.6 ml.
3. Two screw capped test tubes labelled 1 and 2 with graduations at 0.6 ml, 1.2 ml, 1.8 ml, and 2.4 ml.
4. A dropper bottle at least 10 ml in capacity and containing 1 mg of dry 2,6-dichlorophenolindophenol, labelled DCIP and fitted with a dropper graduated at 0.6 ml.
5. A bottle containing a commensurate quantity, such as 10 ml, of distilled water, labelled Water.
6. A packet of vitamin C crystals (10 mg) labelled Vitamin C Crystals.
7. A plastic cup with a wide top, about 5 ml in volume, with a pour lip similar to beaker, labelled Collection Cup.

Such a kit is designed to permit a user to determine whether he or she is getting enough vitamin C in the diet to be able to maintain a continuous excretion of vitamin C in the urine. To be accurate, one should use this test throughout a single 24-hour period, testing a sample at each time of urination, to see whether a sufficient amount of vitamin C is kept in the system to be detected all day long. Because excess vitamin C in the diet may be excreted by the kidneys within 12 hours of reaching the bloodstream, it is important to monitor its presence in the urine during an entire 24-hour period while consuming a typical diet. This kit is designed to allow one to do so safely and conveniently, using a single kit for an entire 24 hour period.

The kit is used as follows. At the start of the 24-hour period during which one intends to test vitamin C excretion, the bottle of water is opened and emptied into the dropper bottle labelled DCIP, and the combined contents are shaken for about 1 minute until all solids are completely dissolved, producing a blue DCIP solution.

A small sample of urine is collected in the Collection Cup each time the individual urinates during the following 24 hours. Test tube 1 is filled up to the level of the first mark (0.6 ml) with the urine so collected. Then all further additions are made to test tube 1.

One dropper full (up to the 0.6-ml mark) of Acid is added to test tube 1, which already contains the urine sample. Next, one dropper full (0.6-ml) of Buffer is added to test tube 1 (up to the 1.2-ml mark). The cap is placed on test tube 1 and the contents are mixed by inverting it at least three times.

The contents of the test tube are then tested to check if there is any vitamin C in the urine. Test tube 1 is opened and one dropper full (0.6 ml) of DCIP solution is added (up to the 1.8-ml mark). If the bluish color of the DCIP solution immediately disappears, vitamin C is present in the urine. If instead a pink color appears and persists for more than 15 seconds, the cap is replaced and the tube inverted several times for mixing. If the pink color now disappears, it is an indication that some vitamin C is excreted in the urine. If the pink color still persists, or if the color cannot be seen clearly because of the color of the urine itself, the procedure is continued as follows.

Half the contents of test tube 1 are poured into test tube 2, so the two solutions are divided approximately evenly between the two tubes. The packet of Vitamin C Crystals is opened and a few crystals (one to three) are sprinkled into test tube 1. The tube is capped and its contents mixed by inverting it at least three times.

The colors of tube 1 and tube 2 are now compared. If the two tubes are identical in color, it is an indication that a sufficient amount of vitamin C is being consumed and that the urine sample being tested contains excess vitamin C. If tube 2 is darker or more strongly pink than tube 1, then it is an indication that no excess is present and that possibly one would benefit from consuming additional vitamin C through a better diet or vitamin supplements.

This test is repeated at each micturition during the chosen 24-hour period. Because vitamin C is excreted rapidly from the body, vitamin C is unlikely to be present in urine more than 16 hours after a good source of vitamin C is last consumed. Therefore, one should check for an entire 24-hour period to determine if enough vitamin C is being consumed on a regular basis to keep a continuously-elevated level in urine.

Note that the kit and procedure just described represent a simple method for implementing the concept of this invention. However, many similar strategies and devices could be used to achieve the same end. For instance, the reagents could be attached in powder form to a stiff, insoluble, plastic stick, such that all of the reagents except the dye would dissolve off of the stick when stirred in a small cup of urine, and then the test stick removed, and the color of the stick would indicate the presence or absence of vitamin C by the change in the dye-containing region of the stick. Note also that certain substances present in the urine of some individuals may interfere with the results of the test. For instance, consumption of beets will turn urine temporarily red, which will make it difficult to observe any results clearly.

A person could use this method, implemented through a product as described above, as a simple indication of whether a sufficient dosage and regimen of a substance were being taken to ensure the presence of a minimum useful excess of the desired substance in the body at all times. The method could similarly be used by researchers to gather data for a variety of substances by age, weight, and other criteria, to establish a dosage which would ensure the presence of a minimum useful excess of a substance in the body. As is known for vitamin C, 60 mg daily will prevent scurvy, but much higher doses may be required to improve health, such as by preventing a variety of adult disorders not readily connected with a lack of vitamin C. By application of the method of the invention, 500 mg of vitamin C twice daily has been determined to provide a sufficient dose to have excess vitamin C excreted. The method may similarly be applied to determine a useful level of aspirin as a blood thinner to prevent heart disease, and for other water-soluble vitamins and minerals such as cystiene, zinc, and selenium, which may be antioxidants, for calcium, and for many other useful substances fitting the three criteria of water solubility, excretion in urine, and nontoxicity at physiologically beneficial levels.

Various other changes in the details, steps and substances that have been described may be made by those skilled in the art within the principles and scope of the invention herein illustrated and defined in the appended claims. Thus, while the present invention has been shown and described herein in what is believed to be the most practical and preferred embodiment, it is recognized that departures can be made therefrom within the scope of the invention, which is not to be limited to the details disclosed herein but is to be accorded the full scope of the claims so as to embrace any and all equivalent apparatus and methods.

I claim:

1. In the oral administration of vitamin C to a person, a method for producing a continuously-saturated level of vitamin C in the body of the person, comprising the following steps:

(a) administering a predetermined dose of vitamin C to the person at a predetermined time;

(b) monitoring the concentration level of vitamin C in the urine of the person to record any increase thereof during a 24-hour period following said predetermined time;

(c) increasing said predetermined dose by a predetermined amount and repeating steps (a) and (b) until a threshold dose is found that produces a sustained increase in said concentration level of vitamin C in the urine of the person for a duration of time at least as long as a predetermined period; and (d) administering no less than said threshold dose of vitamin C to the person at intervals not larger than said duration of time.

2. The method of claim 1, further comprising the step of administering about 500 mg of vitamin C to said person approximately every 12 hours.

* * * * *